United States Patent
Moon

(10) Patent No.: US 11,576,805 B2
(45) Date of Patent: Feb. 14, 2023

(54) MEDICAL FIXATION APPARATUS FOR LESION

(71) Applicant: Byung-Soon Moon, Busan (KR)

(72) Inventor: Byung-Soon Moon, Busan (KR)

(*) Notice: Subject to any disclaimer, the term of this patent is extended or adjusted under 35 U.S.C. 154(b) by 570 days.

(21) Appl. No.: 16/500,794

(22) PCT Filed: Jun. 16, 2017

(86) PCT No.: PCT/KR2017/006317
§ 371 (c)(1),
(2) Date: Oct. 3, 2019

(87) PCT Pub. No.: WO2018/230753
PCT Pub. Date: Dec. 20, 2018

(65) Prior Publication Data
US 2020/0138617 A1    May 7, 2020

(51) Int. Cl.
*A61F 5/058* (2006.01)
*A61F 13/04* (2006.01)

(52) U.S. Cl.
CPC ............ *A61F 5/058* (2013.01); *A61F 13/041* (2013.01)

(58) Field of Classification Search
CPC .......... A61F 5/01; A61F 5/028; A61F 5/0123; A61F 5/0111; A61F 5/05841; A61F 5/0102; A61F 5/0106; A61F 5/0127; A61F 5/02; A61F 2005/0167; A61F 5/0104; A61F 5/022; A61F 5/058; A61F 5/0585; A61F 13/00038; A61F 13/066; A61F 13/08; A61F 2240/002; A61F 5/0113; A61F 5/05; A61F 5/3761; A61F 13/041; A61F 13/023; A61F 13/0276; A61F 13/0289; A61F 2013/00565
See application file for complete search history.

(56) References Cited

U.S. PATENT DOCUMENTS 6,240,923 B1    6/2001    Barrick

FOREIGN PATENT DOCUMENTS

| JP | 2008-272042 | 11/2008 |
|----|-------------|---------|
| JP | 2009-005717 | 1/2009 |
| JP | 5192173 | 5/2013 |
| KR | 10-2005-0114199 | 12/2005 |
| KR | 10-0773862 | 10/2007 |
| KR | 10-2010-0032626 | 3/2010 |
| KR | 10-1050544 | 7/2011 |

(Continued)

OTHER PUBLICATIONS

International Search Report PCT/KR2017/006317 dated Feb. 9, 2018.

(Continued)

*Primary Examiner* — Ophelia A Hawthorne
(74) *Attorney, Agent, or Firm* — Farjami & Farjami LLP

(57) ABSTRACT

The present invention relates to a medical fixation apparatus for a lesion. According to an embodiment, a medical cast comprises: an expansion band having a predetermined length; a pair of elastic fibers which are coupled to opposite widthwise edges of the expansion band, are coated with a water-curable synthetic resin, and can surround a body part; and a plurality of coupling units, which have a flat shape and, when the pair of elastic fibers surround a body part, are arranged at a predetermined interval along an edge at which the pair of elastic fibers face each other to connect the pair of elastic fibers.

2 Claims, 8 Drawing Sheets

(56) References Cited

FOREIGN PATENT DOCUMENTS

| KR | 10-1249749 | 3/2013 |
| KR | 10-1249749 | 4/2013 |
| KR | 10-2013-0083244 | 7/2013 |
| KR | 10-1340561 | 12/2013 |
| KR | 10-2017-0131091 | 11/2017 |
| KR | 20-2017-0004088 | 12/2017 |

OTHER PUBLICATIONS

Notice of Reasons for Refusal dated Oct. 8, 2020 for Application JP 2019-555164.
Decision to Grant a Patent dated Jul. 29, 2021 for Application JP 2019-555164.
First Office Action dated Feb. 3, 2021 for Application CN 201780089077.2.
Extended European Search Report dated Dec. 15, 2020 for EP 17913513.2.

MEDICAL FIXATION APPARATUS FOR LESION

CROSS-REFERENCE TO RELATED APPLICATION

This application is a Section 371 National Stage Application of International Application No. PCT/KR2017/006317, filed Jun. 16, 2017, the contents of which is hereby incorporated by reference in its entirety.

TECHNICAL FIELD

The present invention relates to a medical fixation apparatus for a lesion and, more particularly, a medical fixation apparatus for a lesion such as a cast and a splint that are used to fix a lesion of a body with a fracture, dislocation, a sprain, etc.

BACKGROUND ART

In general, a medical fixation apparatus for a lesion means a medical product such as a plaster cast or a fiberglass cast that is used to fix portions of a body with a fracture, dislocation, a sprain, etc.

Recently, medical fixation apparatuses for a lesion which have various materials and shapes (light and well-ventilated ones are better) have been developed and used for an easy operation and convenience for users (patients).

For example, a cylindrical elastic fiber applied with water-curable synthetic resin (hereafter, referred to as 'related art 1') is representative. Related art 1 is usually sold in a hermetically packed state and the use is as follows.

First, a doctor removes the package and then wets an elastic fiber with water.

Next, the doctor removes moisture from the elastic fiber and puts the elastic fiber on a lesion of a patient like putting on a sock.

Finally the doctor forms the elastic fiber in a predetermined shape before the elastic fiber hardens in order to correctly fix the lesion.

According to related art 1, it is not easy to put the elastic fiber on a lesion due to the adhesion of the water-curable synthetic resin. When curing is finished, it is required to cut the hardened elastic fiber using a saw, but the patient may be frightened in this process. Further, there is a concern of an injury to the skin in the cutting process.

As technology that makes up for the problem of related art 1, there is Korean Patent No. 10-0773862, titled "SPLINT FOR ORTHOPEDICS" (hereafter, referred to as 'related art 2').

Related art 2 is characterized in that the splint for orthopedics is configured such that an extendable band is longitudinally connected to an end of an elastic fiber coated with water-curable synthetic resin on the surface using a connecting means, a coupling means is connected to the other end to form an inlet and an outlet at both ends, the water-curable synthetic resin is coated to be applied to a lesion except for the extendable band and the coupling means are not coated, and the splint can be removed by cutting the extendable band or the coupling means after curing.

In related art 2, the coupling means may be an extendable band, and VELCRO® (a hook-and-loop strap fastener) or a slide fastener may be used.

When an extendable band is used as the coupling means, similar to the related art, it is not easy to put the elastic fiber on a lesion.

When VELCRO® or a slide fastener is used as the coupling means, there are the following problems.

In the process of manufacturing the medial fixation apparatus for a lesion, a process of putting a cast (splint) in a solution containing the water-curable synthetic resin and then squeezing excessive solution by pressing the water-curable synthetic resin with rollers is performed. However, if the VELCRO® or the slide fastener is stained with the water-curable synthetic resin, it may lose its original function, so the VELCRO® or the slide fastener should be covered with a separate vinyl cover etc. Accordingly, the process becomes complicated.

Further, it is difficult to completely seal the VELCRO® or the slide fastener with a vinyl cover, so even though they are covered with a vinyl cover, there is a possibility that the water-curable synthetic resin may permeate through between the vinyl cover and the VELCRO® or the slide fastener during coating.

Further, there is a large concern of damage to the slide fastener when it is pressed by rollers due to the thickness of a zipper pull. Further, the zipper pull of the slide fastener interferes with pressing by rollers, thereby interfering with uniform permeation of the water-curable synthetic resin in the elastic fiber.

Further, there is inconvenience in that it is required to separately remove the vinyl cover for the VELCRO® or the slide fastener during an operation and it is required to take special care in order to prevent the VELCRO® or the slide fastener from being stained with the water-curable synthetic resin.

DISCLOSURE

Technical Problem

An object of the present invention is to provide a medical fixation apparatus for a lesion unlikely to be damaged or have a loss of function in the manufacturing process and that can be easily applied.

Technical Solution

The object of the present invention can be achieved by a medical fixation apparatus for a lesion that includes: an extendable band having a predetermined length; a pair of elastic fiber respectively coupled to both width-directional edges of the extendable band, applied with water-curable synthetic resin, and being able to surround a body part; and a plurality of flat coupler units disposed with predetermined gaps along edges where the pair of elastic fibers face each other to connect the pair of elastic fibers when the body part is surrounded with the pair of elastic fibers.

The object of the present invention can be achieved by a medical fixation apparatus for a lesion that includes: an extendable band having a predetermined length; a pair of elastic fiber respectively coupled to both width-directional edges of the extendable band, applied with water-curable synthetic resin, and being able to surround a body part; a connector, and a plurality of flat coupler units disposed with predetermined gaps along edges where the pair of elastic fibers face each other and having grooves therein in which the connector can be inserted to be connected to each other through the connector when the body part is surrounded with the pair of elastic fibers, in which latchet protrusions are formed at both ends of the connector such that the connector inserted in the coupler units is not unexpectedly removed.

Advantageous Effects

According to the present invention, there is little concern of damage or a loss of function in a manufacturing process and an operation can be easily performed.

MODE FOR INVENTION

Hereafter, various embodiments are described in detail with reference to the accompanying drawings.

First Embodiment

Figure 1:
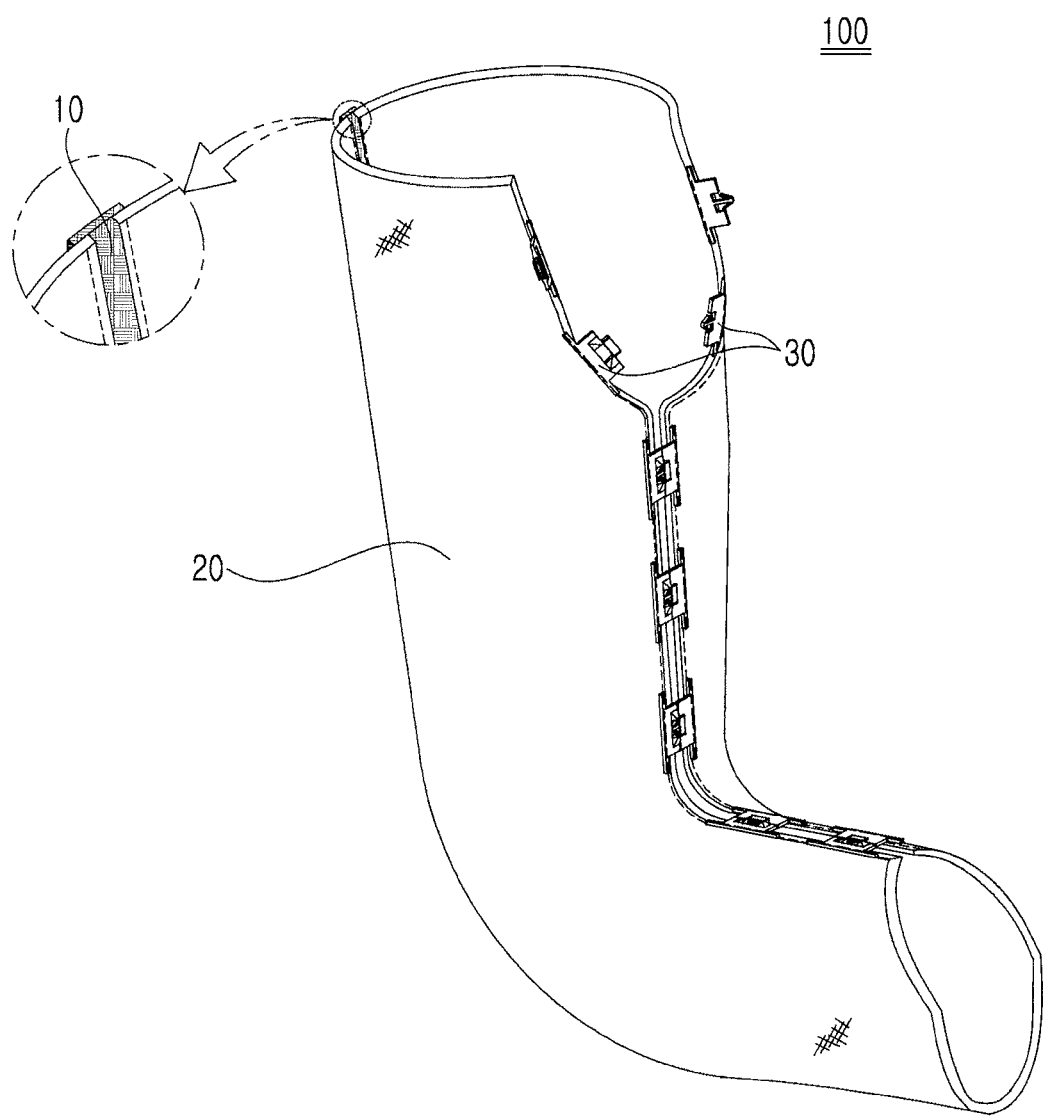
FIG. 1 is a perspective view of a medical fixation apparatus 100 for a lesion according to a first embodiment.

As shown in FIG. 1, a medical fixation apparatus 100 for a lesion according to a first embodiment includes an extendable band 10, elastic fibers 20, and coupler units 30.

The extendable band 10 is made of a rubber material such as Neoprene and has a predetermined width and length. When the medical fixation apparatus 100 for a lesion is applied, the extendable band 10 is usually positioned outside a joint. The extendable band 10 can be easily cut by scissors or a knife, and when curing is finished, the medical fixation apparatus 100 for a lesion can be easily separated by cutting the extendable band 10.

The elastic fiber 20 is provided in pair and they are coupled (sewn) to both width-directional edges of the extendable band 10. Water-curable synthetic resin is applied (permeated) in the fiber tissues of the elastic fiber 20, so when water (moisture) is provided, the elastic fiber 20 hardens. The pair of elastic fibers 20 surrounds a body part with a fracture, dislocation, a sprain, etc. with the extendable band 10 positioned outside a joint therebetween.

That is, when a lesion is surrounded with the elastic fibers 20 wetted with water or sprayed with water, the elastic fibers 20 fix the lesion while hardening.

Further, the elastic fibers 20 may be a polyester knit, a glass fiber knit, a natural fiber, or a synthetic fiber, or may be a knit of natural yarns such as a urethane yarn or a rubber yarn. However, the elastic fiber 20 may be woven in a net shape to be able to elastically extend when they are pulled regardless of the material.

The coupler unit 30 is formed flat, and a plurality of coupler units 30 is provided with predetermined gaps along the edges that face each other when the pair of elastic fibers 20 surrounds a body part and connects the pair of elastic fibers 20 to each other.

In the process of manufacturing the medical fixation apparatus 100 for a lesion, a process of putting the elastic fibers 20 sewn with the coupler units 30 in a solution containing water-curable synthetic resin and then squeezing the solution by pressing the elastic fibers 20 with rollers. However, when the coupler units 30 are formed flat with a thickness similar to the thickness of the elastic fibers 20, the possibility of damage to the coupler units 30 due to rollers is remarkably reduced. Further, the operation of the rollers is not interfered with by the coupler units 30, so the water-curable synthetic resin uniformly permeates into the elastic fibers 20.

The coupler units 30 are composed of male couplers 32 and female couplers 34, and the male couplers 32 and the female couplers 34 are not separated after being fastened, unless they are forcibly damaged. Accordingly, it is possible to easily find out whether the medical fixation apparatus 100 for a lesion has been unexpectedly separated through whether the coupler units 30 have been damaged.

In more detail, the coupler units 40 are made of synthetic resin (plastic etc.) having predetermined elasticity, and may be coupled to the outer side of the elastic fibers 20 not to come in contact with a skin after an operation.

Figure 2:
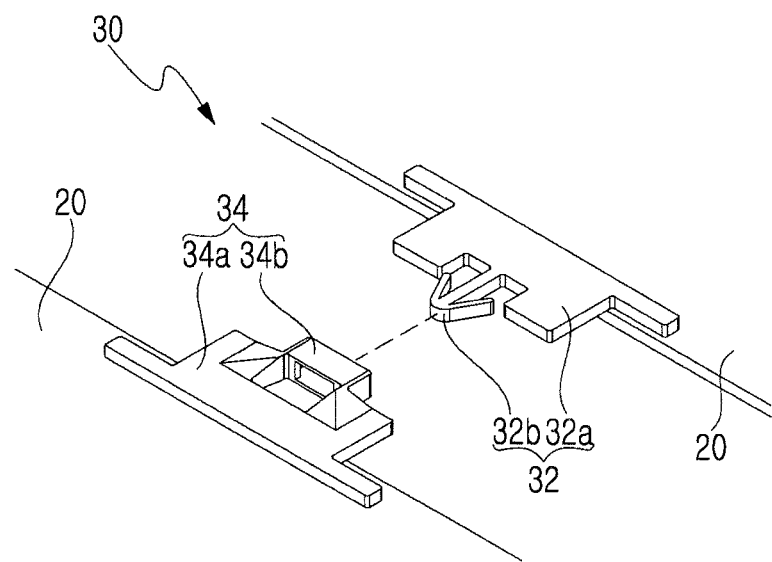
FIG. 2 is a view showing the operation principle of a coupler unit 30 according to the first embodiment.

As shown in FIG. 2, the male coupler 32 is composed of a flat body 32a and a locking portion 32b protruding from a side of the body 32a in a fish spear shape (or an arrow shape), and the female coupler 34 is composed of a flat body 34a and an insertion portion 34b formed on a side of the body 34a and being locked to the locking portion 32b of the male coupler 32.

The width of the rear portion of the locking portion 32b is larger than the width of the insertion portion 34b.

That is, when the male coupler 32 is pushed into the female coupler 34, the rear end of the locking portion 32b is locked and fastened in the insertion portion 34b, and the fastened couplers 32 and 34 are not separated unless the locking portion 32b is forcibly damaged. The coupler units 30 having this configuration normally operate even if they are stained with water-curable synthetic resin. After curing, it is possible to easily separate the coupler units 30 by cutting the locking portions 32b.

On the other hand, unlike VELCRO® or a slide fastener, flows can pass through the spaces between the coupler units 30 having predetermined gaps. Accordingly, the pair of elastic fibers 20 may have lengths such that they do not completely meet each other to improve ventilation.

Figure 3:
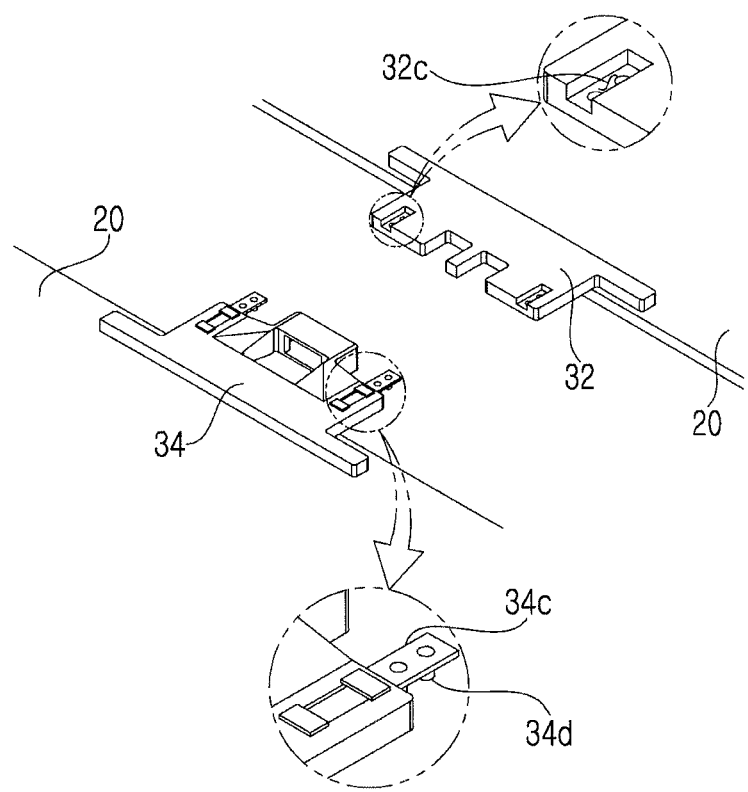
FIG. 3 is a view showing the case when a connection block and an accommodating portion are further formed at the coupler unit 30 according to the first embodiment.

Referring to FIG. 3, a connection block 34c having a locking protrusion 34d on the bottom may be further disposed in the body 34a of the female coupler 34 to be able slide out, and an accommodating portion 32c that can be coupled to the connection block 34c may be further formed at the body 32a of the male coupler 32.

Accordingly, when the splint is unavoidably separated by breaking (cutting) the locking portions 32b of the male couplers 32 due to bathing or additional radiography, the male couplers 32 and the female couplers 34 can be reused.

Second Embodiment

Figure 4:
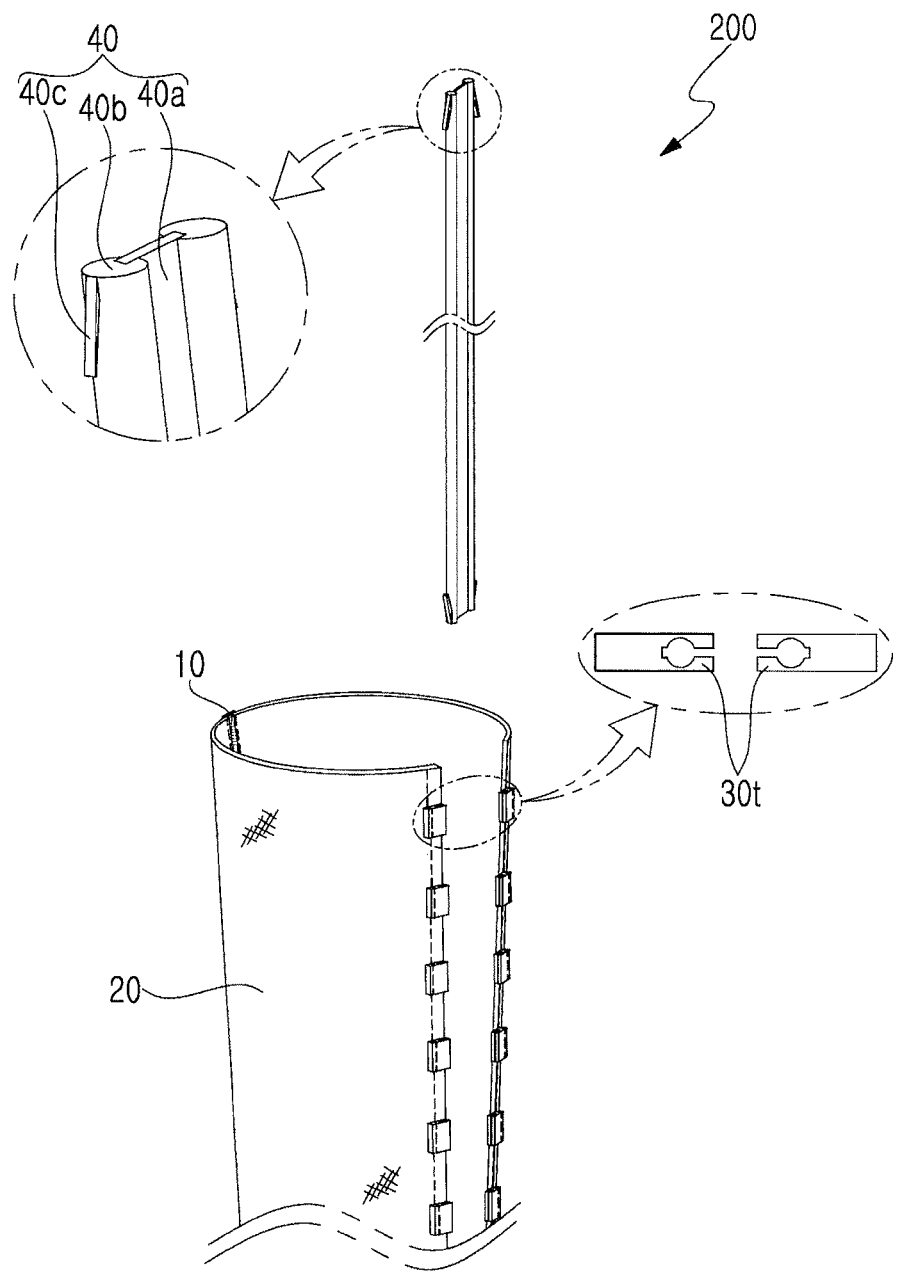
FIG. 4 is a perspective view of a medical fixation apparatus 200 for a lesion according to a second embodiment.

As shown in FIG. 4, a medical fixation apparatus 200 for a lesion according to a second embodiment includes an extendable band 10, elastic fibers 20, coupler units 30t, and a connector 40.

A groove in which the connector 40 can be inserted is formed in the coupler units 30t and the coupler units 30t are connected through the connector 40. The coupler units 30t may be formed as flat and thin as possible.

Latchet protrusions 40c are formed at both end portions of the connector 40 so that the connector 40 inserted in the coupler units 30t is not unexpectedly removed.

As described, when it is required to unavoidably separate the medical fixation apparatus 200 for a lesion and the put it on again, it is possible to pull or reinsert the connector 40 out of or into the coupler units 30t by removing the latchet protrusions 40c with scissors or a knife.

The connector 40 may be composed of a band section 40a made of an elastic fiber and a pair of columns 40b coupled to both width-directional edges of the band section 40a to be inserted into the coupler units 30t.

After an operation, the band section 30a faces the extendable band 10. The band section 40a and the extendable band 40 partially reduce excessive pressure that may be applied to a lesion. After curing, it is possible to easily separate the medical fixation apparatus 200 for a lesion by cutting the band section 40a and the extendable band 40 with a knife or scissors.

According to the medical fixation apparatuses 100 and 200 for a lesion that have the configurations described above, there is little concern of damage to the coupler units 30 and 30t due to rollers in the manufacturing process because they are formed flat.

Further, since the functions of the coupler units 30 and 30t are not largely deteriorated for the structures even if they are stained with water-curable synthetic resin, there is an effect in that it is to possible to easily apply the apparatus to a patient.

Further, it is possible to easily find out whether the cast has been unexpectedly separated through whether the coupler units 30 or the connector 40 has been damaged.

Third Embodiment

Figure 5:
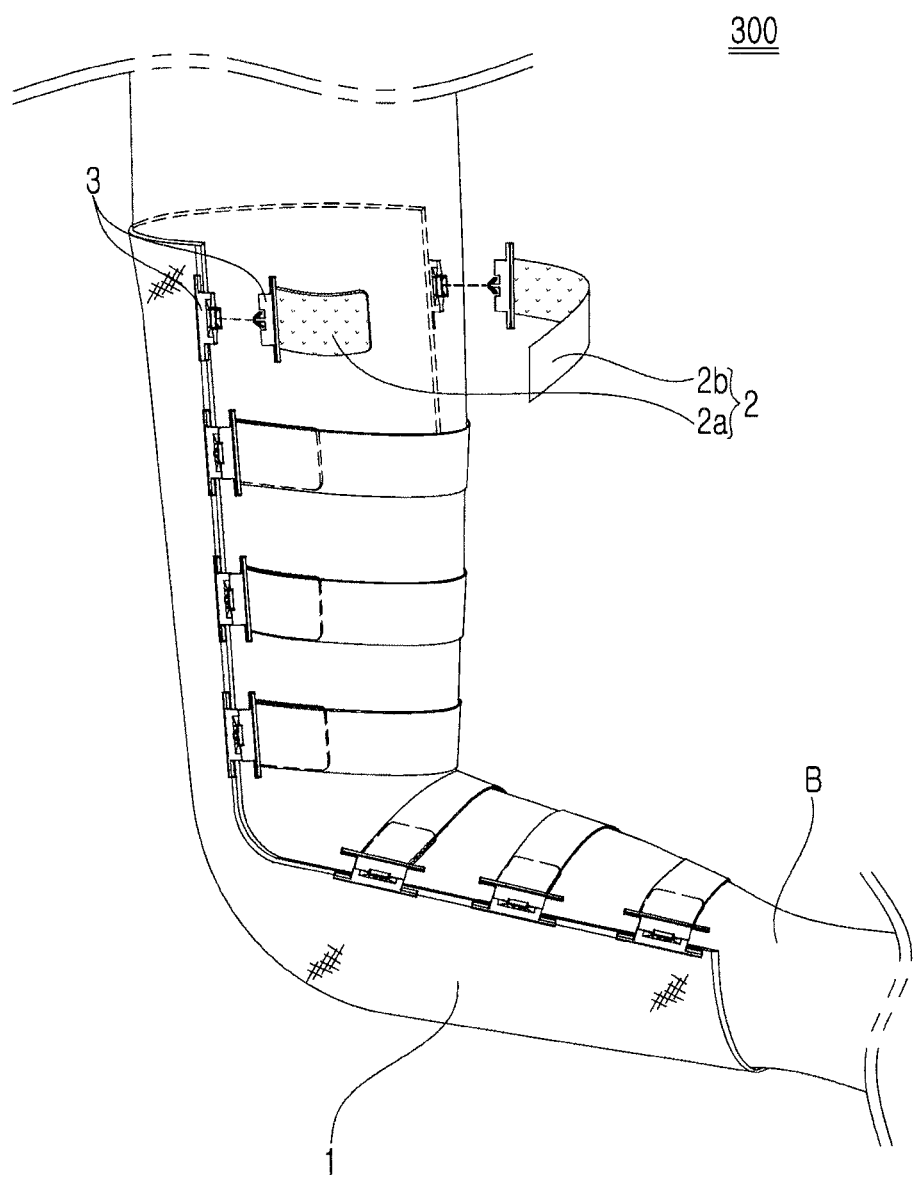
FIG. 5 is a perspective view of a medical fixation apparatus 300 for a lesion according to a third embodiment of the present disclosure.

As shown in FIG. 5, a medical fixation apparatus 300 for a lesion according to a third embodiment includes an elastic fiber 1, a plurality of fixing bands 2, and coupler units 3.

Water-curable synthetic resin has been applied (permeated) between the fiber tissues of the elastic fiber 1, so the water-curable synthetic resin hardens when water (moisture) is applied. The elastic fiber 1 is put on a body part with a fracture, dislocation, a sprain, etc.

That is, when the elastic fibers 1 wetted with water or sprayed with water is brought in close contact with a lesion, the elastic fiber 1 fixes the lesion while hardening.

Further, the elastic fiber 1 may be a polyester knit, a glass fiber knit, a natural fiber, or a synthetic fiber, or may be a knit of natural yarns such as a urethane yarn or a rubber yarn. However, the elastic fiber 20 may be woven in a net shape to be able to elastically extend when they are pulled regardless of the material The fixing bands 2 can be adjusted in length and are coupled to the elastic fiber 1 by the coupler units 3 to be described below. It is possible to easily apply the medical fixation apparatus 300 for a lesion by putting the elastic fiber 1 on an injured body B and the coupling the fixing bands 2 to the elastic fiber 1. Further, the fixing bands 2 are not coupled to the elastic fiber 1 and are separately sold, so there is no concern that the fixing bands 2 lose their functions (VELCRO® function etc.) by being soaked in water-curable synthetic resin in the manufacturing process.

The fixing bands 2 are each composed of a first band 2a with a VELCRO® portion on the front and a second band 2b with a VELCRO® portion on the bottom, and the first and second bands 2a and 2b are combined in a single unit.

According to common medical casts, it is required to prevent a patient from freely separating the medical casts, but a medical fixation apparatus for a lesion that is temporarily put on before a cast is applied may be formed in a structure that can be freely separated to be able to check the state (swelling) of a lesion.

Figure 6:
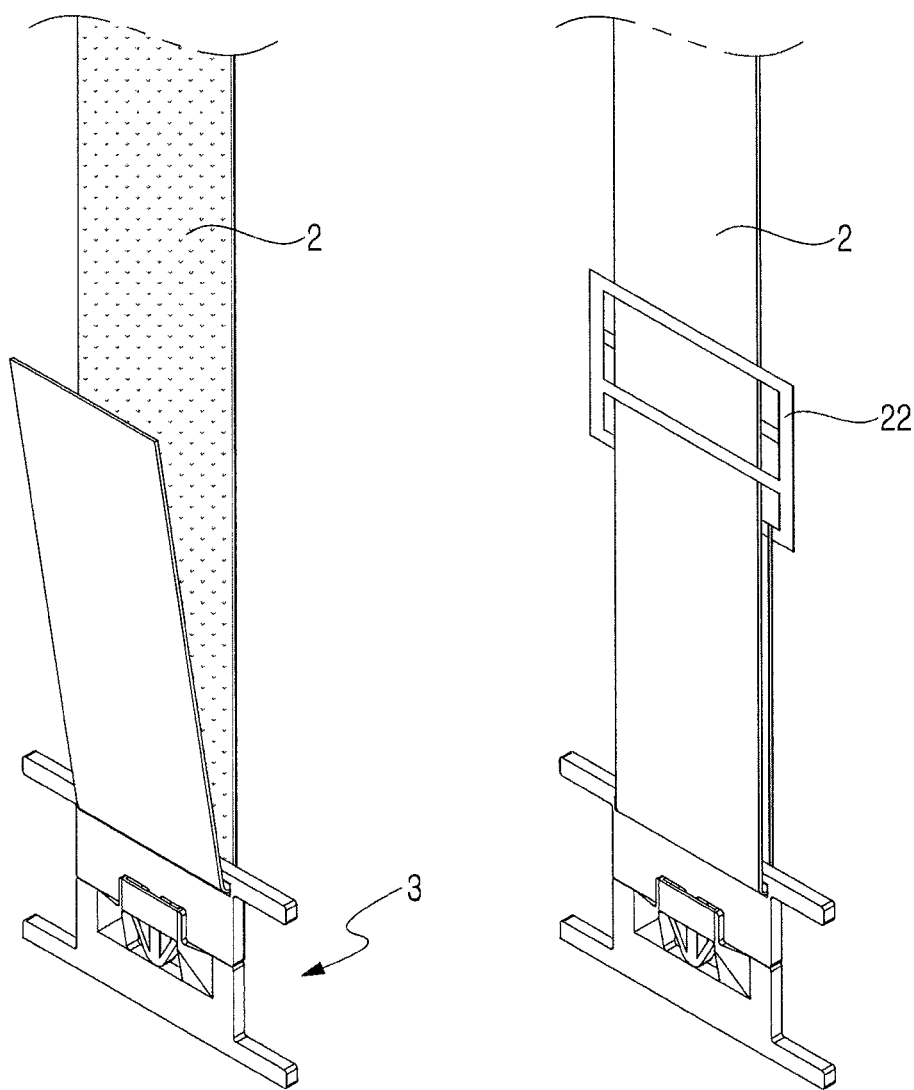
FIG. 6 is a view showing various modifications of a fixing band 2 according to the third embodiment of the present disclosure.

On the other hand, as shown in FIG. 6, the fixing band 2 may be VELCRO® having an adjustable length (FIG. 6A), and or may have an additional separate length adjuster 22 such as a buckle (FIG. 6B).

Further, when the fixing band 2 is made of an elastic rubber material, the length may not need to be adjusted.

The coupler unit 3 is formed flat with a thickness similar to the thickness of the elastic fiber 1 and is disposed at a width-directional edge of the elastic fiber 1, an end of the fixing band 2, the other edge of the elastic fiber 1, and the other end of the fixing band 2 so that the elastic fiber 1 placed on a lesion can be fixed by a plurality of fixing bands.

In the process of applying (coating) water-curable synthetic resin to the elastic fiber 1, a process of putting the elastic fiber 1 sewn with the coupler units 3 in a solution containing water-curable synthetic resin and then squeezing the solution by pressing the elastic fiber 1 with rollers. However, when the coupler units 3 are formed flat with a thickness similar to the thickness of the elastic fiber 1, the possibility of damage to the coupler units 3 due to rollers is remarkably reduced. Further, the operation of the rollers is not interfered with the coupler units 3, so the water-curable synthetic resin uniformly permeates into the elastic fiber 1.

Figure 7:
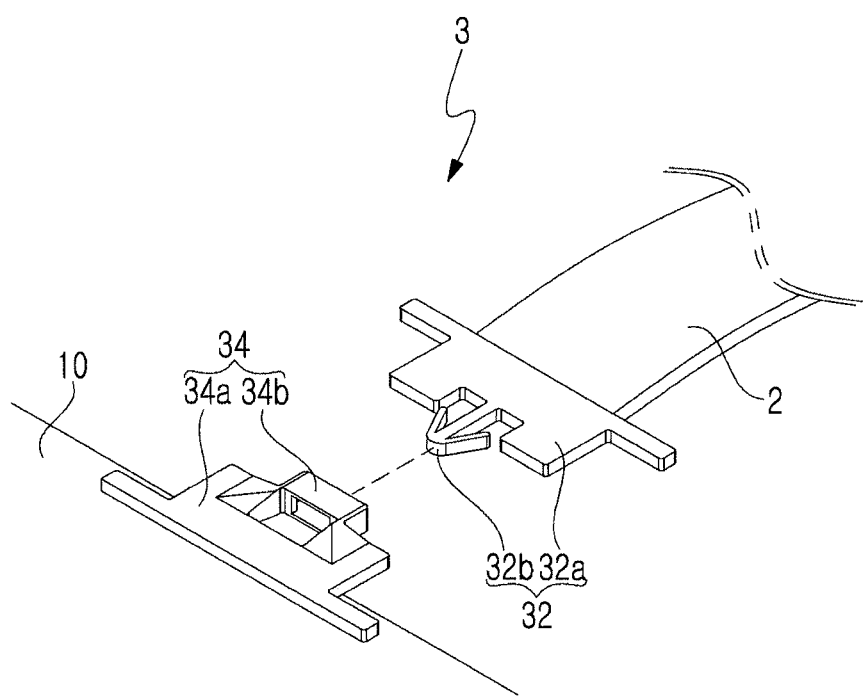
FIG. 7 is a view showing the operation principle of a coupler unit 3 according to the third embodiment of the present disclosure.

As shown in FIG. 7, the coupler unit 3 is composed of a male coupler 32 and a female coupler 34.

The male coupler 32 is composed of a flat body 32a and a locking portion 32b protruding from a side of the body 32a in a fish spear shape (or an arrow shape), and the female coupler 34 is composed of a flat body 34a and an insertion portion 34b formed on a side of the body 34a and being locked to the locking portion 32b of the male coupler 32.

The width of the rear end of the locking portion 32b is larger than the width of the insertion portion 34b. That is, when the male coupler 32 is pushed into the female coupler 34, the rear end of the locking portion 32b is locked and fastened in the insertion portion 34b.

The coupler unit 3 may be made of synthetic resin (plastic etc.) having predetermined elasticity and may be coupled to the outer side of the elastic fiber 10 not to be in contact with a skin after an operation.

Further, when the female couplers 34 are disposed at both edges of the elastic fiber 1 and the male couplers 32 are disposed at both ends of the fixing band 2, there is an effect in that it is possible to more easily apply the medical fixation apparatus 300 for a lesion.

The coupler unit 3 having the structure described above normally operates even if it is stained with water-curable synthetic resin. Accordingly, there is no need for covering the couplers (32 or 34) on the elastic fiber 1 with a separate vinyl in the process of applying (coating) water-curable synthetic resin to the elastic fiber 1. Further, there is no need for taking special care to prevent the coupler unit 3 from being stained with synthetic resin during an operation.

Fourth Embodiment

Figure 8:
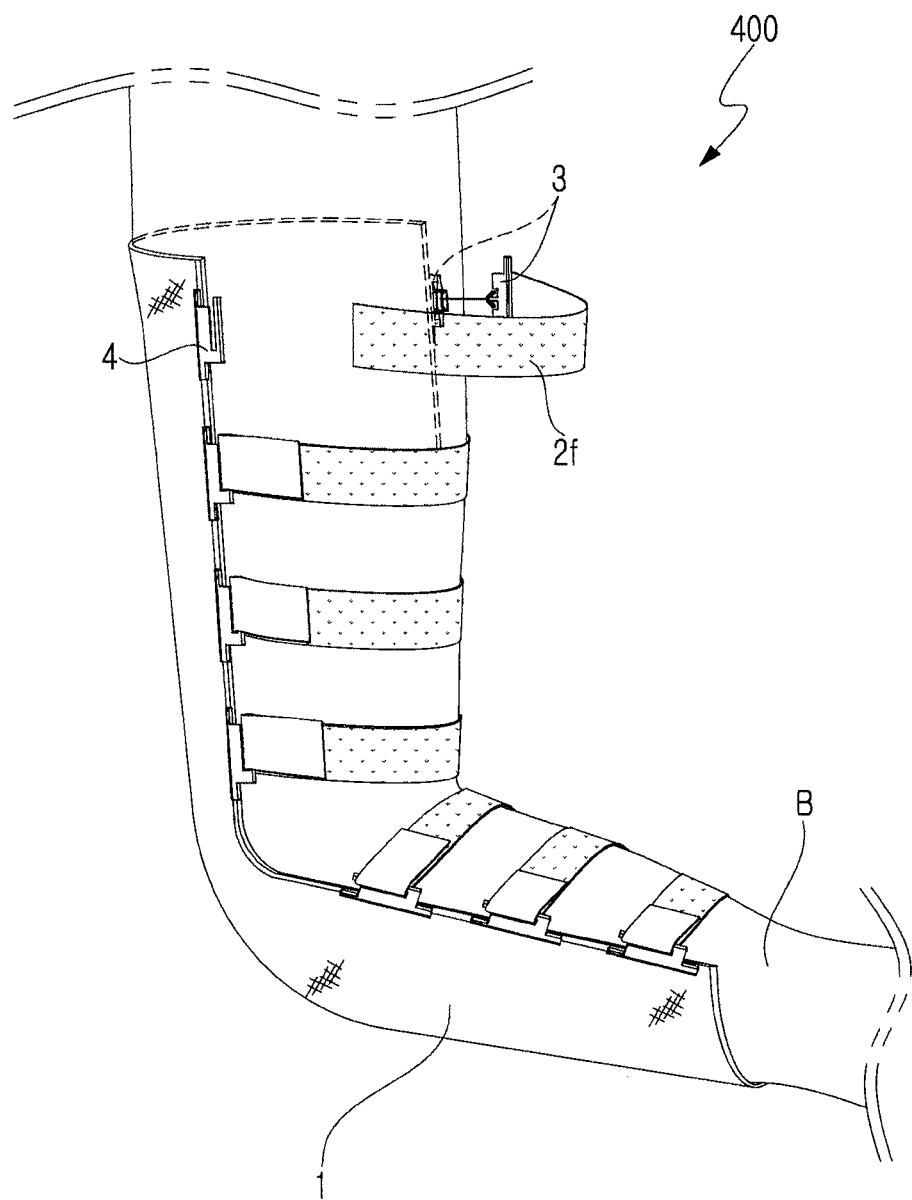
FIG. 8 is a perspective view of a medical fixation apparatus 400 for a lesion according to a fourth embodiment of the present disclosure.

As shown in FIG. 8, a medical fixation apparatus 400 for a lesion according to a third embodiment includes an elastic fiber 1, a plurality of fixing bands 2, and coupler units 3.

A plurality of hooks 4 is disposed at a width-directional edge of the elastic fiber 1. The hooks 4 are formed flat with a thickness similar to the thickness of the elastic fiber 1 and allow fixing bands 2*f* to be hooked.

The fixing bands 2*f* have a VELCRO® portion on the front.

The coupler unit 3 is disposed at the other width-directional edge of the elastic fiber 1 and an end of the fixing band 2*f* such that the end of the fixing band 2*f* can be coupled to the elastic fiber 1.

Figure 9:
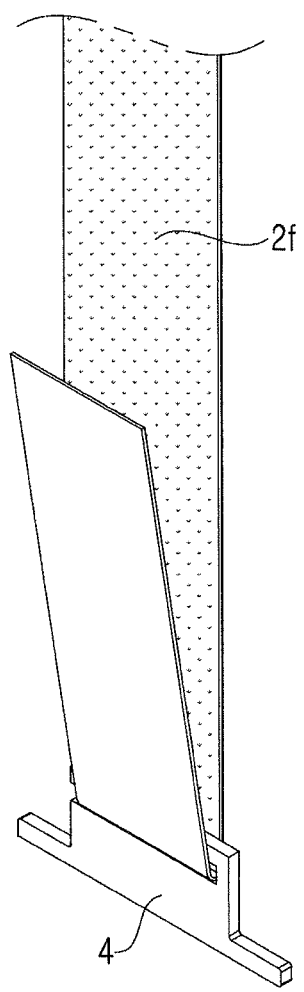
FIG. 9 is a view showing the use of a fixing band 2f according to the fourth embodiment of the present disclosure.

As shown in FIGS. 8 and 9, an end of the fixing band 2*f* is coupled to the elastic fiber 1 by the coupler unit 3 and the other end is around the hook 4 and then coupled to a predetermined position of the fixing band 2*f*.

According to the medical fixation apparatuses 300 and 400 for a lesion that have the configurations described above, the coupler unit 3 is formed flat with a thickness similar to the thickness of the elastic fiber 1, so there is little concern of damage in a process of rolling the elastic fiber 1.

Further, since the coupler unit 3 does not interfere with rolling, a product with water-curable synthetic resin uniformly applied (coated) to the elastic fiber 1 can be manufactured.

Further, since the function of the coupler unit 3 is not largely deteriorated even if it is stained with water-curable synthetic resin, there is no need for covering the coupler unit 3 with a separate vinyl cover in the manufacturing process and the apparatus can be easily applied to a patient.

<Description of the Reference Numerals in the Drawings>

| | |
|---|---|
| 100, 100': Medical fixation apparatus for a lesion | 10: Extendable band |
| 20: Elastic fiber | 30, 30': Coupler unit |
| 32: Male coupler | 32a: Body |
| 32b: Locking portion | 32c: Accommodating portion |
| 34: Female coupler | 34a: Body |

<Description of the Reference Numerals in the Drawings>

| | |
|---|---|
| 34b: Insertion portion | 34c: Connection block |
| 34d: Locking protrusion | 40: Connector |
| 40a: Band section | 40b: Column |
| 40c: Latchet protrusion | |

The invention claimed is:

1. A medical fixation apparatus comprising:
   an extendable band having a predetermined length;
   a pair of elastic fibers respectively coupled to both width-directional edges of the extendable band, applied with water-curable synthetic resin, and being able to surround a body part; and
   a plurality of flat coupler units disposed on the pair of elastic fibers with predetermined gaps therebetween and along edges where the pair of elastic fibers face each other to connect the pair of elastic fibers when the body part is surrounded with the pair of elastic fibers;
   wherein each of the plurality of coupler units is composed of a male coupler and a female coupler that are made of a material having a predetermined elasticity,
   the male coupler is composed of a first flat body and a locking portion protruding from a side of the first flat body in a fish spear shape,
   the female coupler is composed of a second flat body and an insertion portion formed on a side of the second flat body and being locked to the locking portion, and
   a width of a rear end of the locking portion is larger than a width of the insertion portion, and the male coupler and the female coupler are not separated after being fastened to each other;
   wherein a connection block having a locking protrusion on a bottom is further disposed in the second flat body of the female coupler to be able slide out, and
   an accommodating portion configured to be coupled to the connection block is further formed at the first flat body of the male coupler.

2. The medical fixation apparatus of claim 1, wherein the plurality of coupler units are coupled to an outer side of the pair of elastic fibers, such that when the body part is surrounded with the pair of elastic fibers, the plurality of coupler units do not come in contact with a skin of the body part.

* * * * *